United States Patent
Ganguly-Mink et al.

(10) Patent No.: US 10,676,430 B2
(45) Date of Patent: Jun. 9, 2020

(54) NON-ALPHA SUBSTITUTED PEROXY ACIDS AND USES THEREOF

(71) Applicant: Stepan Company, Northfield, IL (US)

(72) Inventors: Sangeeta Ganguly-Mink, Chicago, IL (US); Kenneth J. Littel, Hawthorn Woods, IL (US); Shui Ping Zhu, Phoenixville, PA (US)

(73) Assignee: Stepan Company, Northfield, IL (US)

( * ) Notice: Subject to any disclaimer, the term of this patent is extended or adjusted under 35 U.S.C. 154(b) by 0 days.

(21) Appl. No.: 16/135,854

(22) Filed: Sep. 19, 2018

(65) Prior Publication Data

US 2019/0016678 A1  Jan. 17, 2019

Related U.S. Application Data

(63) Continuation of application No. PCT/US2017/023397, filed on Mar. 21, 2017.

(60) Provisional application No. 62/311,506, filed on Mar. 22, 2016.

(51) Int. Cl.

| C07C 409/24 | (2006.01) |
|---|---|
| A01N 37/16 | (2006.01) |
| A01N 37/36 | (2006.01) |
| C11D 3/39 | (2006.01) |
| A01N 59/00 | (2006.01) |
| C11D 3/48 | (2006.01) |
| A61L 2/18 | (2006.01) |
| C07C 407/00 | (2006.01) |
| C11D 1/62 | (2006.01) |
| C11D 1/72 | (2006.01) |

(52) U.S. Cl.
CPC ............ *C07C 409/24* (2013.01); *A01N 37/16* (2013.01); *A01N 37/36* (2013.01); *A01N 59/00* (2013.01); *A61L 2/18* (2013.01); *A61L 2/186* (2013.01); *C07C 407/00* (2013.01); *C11D 1/62* (2013.01); *C11D 1/72* (2013.01); *C11D 3/39* (2013.01); *C11D 3/3945* (2013.01); *C11D 3/3947* (2013.01); *C11D 3/48* (2013.01)

(58) Field of Classification Search
CPC ........ A01N 37/36; A01N 59/00; A01N 37/02; A01N 37/16; C07C 407/00; C07C 409/24; C11D 1/62; C11D 1/72; C11D 3/39; C11D 3/3945; C11D 3/3947; C11D 3/48; A61L 2/18; A61L 2/186
See application file for complete search history.

(56) References Cited

U.S. PATENT DOCUMENTS

| 5,200,189 | A | 4/1993 | Oakes et al. |
|---|---|---|---|
| 5,545,374 | A * | 8/1996 | French ................ A01N 37/16 422/28 |
| 6,294,186 | B1 * | 9/2001 | Beerse ................ A01N 43/36 424/401 |
| 6,627,594 | B1 * | 9/2003 | James ................ A01N 37/36 510/310 |
| 8,758,789 | B2 | 6/2014 | Man et al. |
| 8,877,254 | B2 | 11/2014 | Li et al. |
| 8,957,246 | B2 | 2/2015 | McSherry et al. |
| 9,288,982 | B2 | 3/2016 | McSherry et al. |
| 2002/0197293 | A1 | 12/2002 | D'Ambrogio et al. |
| 2004/0033269 | A1 * | 2/2004 | Hei ................ A01N 25/02 424/616 |
| 2010/0143491 | A1 | 6/2010 | Kawabata et al. |
| 2011/0318461 | A1 | 12/2011 | Ho |
| 2012/0213835 | A1 | 8/2012 | Neas et al. |
| 2014/0120179 | A1 | 5/2014 | Smith et al. |

FOREIGN PATENT DOCUMENTS

| JP | 2007260132 | 10/2007 |
|---|---|---|
| JP | 2007267811 | 10/2007 |
| WO | WO00/66079 | 11/2000 |
| WO | 0076963 | 12/2000 |
| WO | 2006068306 | 6/2006 |

OTHER PUBLICATIONS

International Bureau, "International Preliminary Report on Patentability," issued in connection with International Application No. PCT/US2017/023397, dated Sep. 25, 2018, 7 pages.
International Search Report; and Written Opinion of the International Searching Authority for International Application No. PCT/US2017/023397 dated Jun. 9, 2017.
European Patent Office, "Extended European Search Report," issued in connection with European Patent Application No. 17770980.5, dated Jul. 16, 2019, 11 pages.
Yuan et al., "Oxygen Donation to Manganese (III) Tetraphenylporphyrin Chloride. Low Reactivity of Hydroperoxides as Oxygen Donors to Manganese (III) Porphyrins," Inorganic Chemistry, vol. 24, No. 7, Mar. 1, 1985, 2 pages.

\* cited by examiner

*Primary Examiner* — Jafar F Parsa
*Assistant Examiner* — Blaine G Doletski
(74) *Attorney, Agent, or Firm* — McAndrew, Held & Malloy, Ltd.

(57) ABSTRACT

The present disclosure is related to non-alpha-substituted, low molecular weight peracid compositions. The peracids have no or a negligible amount of odor, have good stability, and have antimicrobial properties. The peracid compositions can be formulated into a wide variety of end use products, including disinfectants, sanitizers, sporicides, fungicides, laundry products, hard surface cleaners, bleaching agents, personal cleansers, and water treatment products.

18 Claims, No Drawings

NON-ALPHA SUBSTITUTED PEROXY ACIDS AND USES THEREOF

RELATED APPLICATIONS

This a continuation of and claims priority to PCT Patent Application PCT/US17/23397 having an International filing date of Mar. 21, 2017, which claims priority to U.S. Provisional Application No. 62/311,506, filed Mar. 22, 2016. The contents of the applications referred to above are hereby incorporated by reference.

FIELD OF THE INVENTION

The present technology relates to compositions comprising low molecular weight peroxycarboxylic acids having a substituent group on a carbon atom that is not the alpha carbon, i.e., not adjacent to the carbonyl carbon. The present technology further relates to methods of manufacture/formation and uses for such compositions.

BACKGROUND OF THE INVENTION

The organic peroxyacid, peracetic acid (PAA) has found wide application as an antimicrobial in fields such as hard surface disinfection, direct food sanitization, food contact surface sanitization, bacterial and slime control in water systems such as cooling tower water, oil field, pulp and paper, and odor control in waste water treatment. In general, smaller molecular and water soluble peroxyacids, such as peracetic acid, perpropionic or perpropanoic acid, perbutanoic acid, and perpentanoic acid, can provide antimicrobial performance, but all have the drawback of possessing an offensive or unpleasant odor profile. Bigger molecular peracids, such as perhexanoic acid, perheptanoic acid, and peroctanoic acid, offer a reduction in offensive smell, but possess reduced water solubility that necessitates the use of solubilizing agents, such as surfactants, and/or solvents, and/or coupling agents, while still providing antimicrobial performance. One drawback of such solubilizing agents is that they can decrease the chemical stability of the peroxyacid. Peroxyacids having a substituent group on the alpha carbon, such as perglycolic acid, perlactic acid, or perpyruvic acid, have a reduced odor and also provide some antimicrobial properties. However, such compounds are not stable due to incompatibility of the substituent group, such as hydroxyl, ketone, or the like, with the peracid group. Such instability/incompatibility has prevented use of such peroxyacids in practice.

There is therefore a need for a low molecular weight and water soluble peracid that has a reduced unpleasant odor profile, provides good antimicrobial performance, and is chemically stable so that it can be used in a wide variety of formulations and applications.

SUMMARY OF THE INVENTION

The present technology relates to compositions comprising a non-alpha substituted peroxy acid having the following Formula 1 or Formula 2, or mixtures thereof:

$$X\text{—}(C_nH_{2n})CH_2COOOH \qquad \text{Formula 1}$$

where n=1 to 6
$C_nH_{2n}$ is linear or branched, saturated or unsaturated
($C_nH_{2n}$ is $C_nH_{2n-2}$ when Formula 1 is unsaturated)
X can be attached to any carbon in the $C_nH_{2n}$ group (or $C_nH_{2n-2}$ if unsaturated) and is selected from F, Cl, Br, I, OH, $OCH_3$, $OC_2H_5$, SH, $N(CH_3)_2$, $NH(CH_3)$, $N(CH_2CH_2OH)_2$, $NH(CH_2CH_2OH)$, RCOO, RCO, $SO_3(M^{m+})_{1/m}$, or $PO_3(M_{1/m}{}^{m+})_2$ expressed as below:

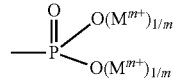

where R is an alkyl group with 1 to 3 carbon atoms, M is H, ammonium, or a metal or earth metal ion and m is 1-4.

$$X\text{—}(C_yH_{2y-1})CHCOOOH \qquad \text{Formula 2}$$

where y=2 to 6
$C_yH_{2y-1}$ forms a saturated or unsaturated ring ($C_yH_{2y-1}$ is $C_yH_{2y-3}$ when Formula 2 is unsaturated)
X can be attached to any carbon in the $C_yH_{2y-1}$ group (or $C_yH_{2y-3}$ if unsaturated) and is selected from F, Cl, Br, I, OH, $OCH_3$, $OC_2H_5$, SH, $N(CH_3)_2$, $NH(CH_3)$, $N(CH_2CH_2OH)_2$, $NH(CH_2CH_2OH)$, RCOO, RCO, $SO_3(M^{m+})_{1/m}$, or $PO_3(M_{1/m}{}^{m+})_2$, expressed as below:

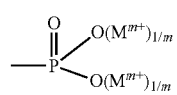

where R is an alkyl group with 1 to 3 carbon atoms, M is H, ammonium, or a metal or earth metal ion, and m is 1-4.

The present technology also relates to compositions comprising the peroxy acid of Formula 1 or Formula 2 or mixtures thereof.

DETAILED DESCRIPTION

As used herein, "peracid" or "peroxy acid" means an organic acid having the carboxylic (—COOH) group oxidized to a percarboxylic group (—COOOH). The peracids described herein are organic peracids.

"Antimicrobial" refers to an agent having effectiveness for controlling the growth of, reducing, and/or killing microbes, such as bacteria, virus, fungi, yeast, algae, cyanobacteria, archaea, prions etc. Antimicrobial further refers to agents capable of controlling odor caused by microorganisms.

"Disinfectant" and "Sanitizes" refer to an agent, product, or composition that is applied onto objects to reduce and/or destroy microorganisms that are living on the objects.

A "ready-to-use" or "RTU" product, composition, or formulation in the present application refers to a product, composition, or formulation that is ready to be applied to articles or surfaces to be disinfected or sanitized.

A "dilutable," "concentrate," or "dilutable concentrate" product, composition, or formulation in the present application refers to a product, composition, or formulation that needs to be diluted with a diluent (e.g., water) in a ratio of, for example, but not limited to, 1:256, 1:128, 1:64, or 1:32, before it can be applied to articles, substrates, or surfaces to be biocidally treated, sanitized or disinfected.

As used herein, "reduced odor" means less odor than peracetic acid, which has a sharp, pungent odor.

As used herein, a "low odor" or "negligible odor" peracid is a peracid that a typical person can barely detect by smell.

The present technology relates to low molecular weight non-alpha-substituted water soluble/miscible peroxy acids having the structure of Formula 1 or Formula 2, or mixtures thereof:

$$X\text{—}(C_nH_{2n})CH_2COOOH \quad \text{Formula 1}$$

where n=1 to 6
$C_nH_{2n}$ is linear or branched saturated or unsaturated
($C_nH_{2n}$ is $C_nH_{2n-2}$ when Formula 1 is unsaturated)
X can be attached to any carbon in the $C_nH_{2n}$ group (or $C_nH_{2n-2}$ if unsaturated) and is selected from F, Cl, Br, I, OH, $OCH_3$, $OC_2H_5$, SH, $N(CH_3)_2$, $NH(CH_3)$, $N(CH_2CH_2OH)_2$, $NH(CH_2CH_2OH)$, RCOO, RCO, $SO_3(M^+)_{1/m}$ or $PO_3(M_{1/m}^{m+})_2$, expressed as below:

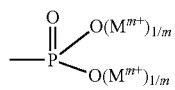

where R is an alkyl group with 1 to 3 carbon atoms, M is H or ammonium, or metal or earth metal ion, and m is 1-4, preferably 1-2, more preferably 1.

$$X\text{—}(C_yH_{2y-1})CHCOOOH \quad \text{Formula 2}$$

y=2 to 6
$C_yH_{2y-1}$ forms a saturated or unsaturated ring ($C_yH_{2y-1}$ is $C_yH_{2y-3}$ when Formula 2 is unsaturated)
X can be attached to any carbon in the $C_yH_{2y-1}$ group ($C_yH_{2y-3}$ if unsaturated) and is selected from F, Cl, Br, I, OH, $OCH_3$, $OC_2H_5$, SH, $N(CH_3)_2$, $NH(CH_3)$, $N(CH_2CH_2OH)_2$, $NH(CH_2CH_2OH)$, RCOO, RCO, $SO_3(M^+)_{1/m}$ or $PO_3(M_{1/m}^{m+})_2$, expressed as below:

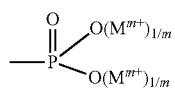

where R is an alkyl group with 1 to 3 carbon atoms, and M is H, ammonium, or a metal or earth metal ion, and m is 1 to 4, preferably 1 to 2, more preferably 1. In some embodiments, n is from 1 to 4 in Formula 1. In some embodiments, X is Cl, OH or $OCH_3$.

Surprisingly, the peroxy acids of Formula 1 and 2 are odorless or have significantly reduced odor compared to traditional peroxy acids, such as peracetic acid, perpropionic acid, perbutanoic acid, and perpentanoic acid. The peroxy acids of the present technology also provide good antimicrobial efficacy without the need for solubilizing agents, such as surfactants, solvents and/or coupling agents. Further, such peroxy acids are more chemically stable than alpha-substituted peracids, such as perglycolic acid, perlactic acid, and perpyruvic acid. Without being bound by theory, it is believed that, when the substituent group is attached to a non-alpha carbon, there is less interaction between the substituent group and the peroxy group because of the greater separation between the two groups, which could lead to better chemical stability. The peroxy acids of the present technology can be used as an antimicrobial agent, a disinfectant, a sanitizer, a deodorizer, a bleaching agent, or a cleaner in a wide variety of applications, including hard surface disinfection, direct food sanitization and cleaning, food contact surface sanitization, laundry applications, soft surface treatment, personal products such as skin and hair care, and for microorganism and odor control in industrial and recreational water systems.

In one embodiment, when X is OH and n is 1 in Formula 1, the peroxy acid is 3-hydroxyperpropionic acid (3-HPPA). 3-HPPA has been found to have negligible odor, antimicrobial properties, and is less combustible than peracetic acid, making it useful for applications where peracetic acid is used, such as direct food or non-food sanitization or disinfection areas.

The peroxy acids of the present technology are made by a reaction between the corresponding non-alpha substituted carboxylic acid and hydrogen peroxide, or other peroxide source, in an aqueous medium, with or without an acid catalyst. Suitable peroxide sources for use herein include hydrogen peroxide, perborate, persulfate, percarbonate, perphosphate, sodium peroxide, magnesium peroxide, calcium peroxide, and others known to those skilled in this art. Preferably an acid catalyst is used in order to shorten the reaction time between the carboxylic acid and the peroxide. Suitable acid catalysts include, for example, sulfuric acid ($H_2SO_4$), methanesulfonic acid ($CH_3SO_3H$), hydrochloric acid (HCl), and nitric acid ($HNO_3$). Sulfuric acid is preferred, preferably at an amount of ≤1% by weight of the total mixture. One reaction scheme for preparing the peroxy acid is shown below with reference to a peroxy acid of Formula 1:

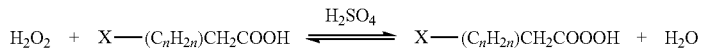

where X and n have the same meanings recited above. It will be appreciated that a similar reaction scheme can be used to generate a peroxy acid of Formula 2. The reaction can be carried out at room temperature (25° C.) or below, such as down to −10° C. or the freezing point of the formulation, depending on the levels of each ingredient.

In the above reaction scheme, the peroxy acid is present in the resulting mixture in a concentration that is in equilibrium with the corresponding carboxylic acid, hydrogen peroxide, and water. Non-alpha substituted carboxylic acids and peroxides are commercially available in different concentrations. One of skill in the art can easily determine the appropriate starting amounts of carboxylic acid and peroxide for the reaction, based on the concentration of each starting material and the desired concentration for the resulting peroxy acid. In general, a suitable amount of non-alpha substituted carboxylic acid is in the range of about 20% to about 50% by active weight based on the total weight of the starting reaction mixture, and a suitable amount of peroxide is in the range of about 8% to about 35% by active weight. For example, in one embodiment, about 20% by active weight 3-HPA is reacted with about 8% by active weight $H_2O_2$ in the presence of 1% $H_2SO_4$ catalyst to generate about 1% 3-HPPA. The following table provides exemplary amounts of starting reactants based on their starting concentrations and desired concentration of resulting 3-HPPA.

TABLE 1

Various reagent inputs to generate targeted peracid of 3-HPPA

| Targets | Ways to make designed 3-HPPA | 3-HPA w % | purity | H₂O₂ w % | purity | %, H₂SO₄ (96%) | Water % added | ===> | 3-HPPA % | Water % formed |
|---|---|---|---|---|---|---|---|---|---|---|
| Target: 1.0% 3-HPPA | Scenario I: designed | 20.00 | 100.0% | 8.00 | 100.0% | 1.00 | 71.00 | | 0.00 | |
| | Scenario II: operational | 66.67 | 30.0% | 16.00 | 50.0% | 1.00 | 16.33 | | 0.00 | |
| | Scenario III: operational | 33.33 | 60.0% | 22.86 | 35.0% | 1.00 | 42.81 Exist | | 0.00 | |
| | Final composition | 19.15 | | 7.68 | | 1.00 | 71.00 | ===> | 1.00 | 0.17 |
| Target: 3.5% 3-HPPA | Scenario I: designed | 49.00 | 100.0% | 8.00 | 100.0% | 1.00 | 42.00 | | 0.00 | |
| | Scenario II: operational | 81.67 | 60.0% | 16.00 | 50.0% | 1.00 | 1.33 | | 0.00 | |
| | Scenario III: operational | 61.25 | 80.0% | 22.86 | 35.0% | 1.00 | 14.89 Exist | | 0.00 | |
| | Final composition | 46.03 | | 6.88 | | 1.00 | 42.00 | ===> | 3.50 | 0.59 |
| Target: 7.5% 3-HPPA | Scenario I: designed | 24.50 | 100.0% | 35.00 | 100.0% | 1.00 | 39.50 | | 0.0% | |
| | Scenario II: operational | 40.83 | 60.0% | 50.00 | 70.0% | 1.00 | 8.17 | | 0.0% | |
| | Scenario III: operational | 28.82 | 85.0% | 70.00 | 50.0% | 1.00 | 0.18 Exist | | 0.0% | |
| | Final composition | 18.13 | | 32.59 | | 1.00 | 39.50 | ===> | 7.50 | 1.27 |

In addition to the acid catalyst, stabilizers, such as sodium stannate can optionally be added to the reaction mixture to stabilize the hydrogen peroxide and peroxy acid and prevent decomposition of these components. The stabilizers can be included as part of a mixture with the hydrogen peroxide component, added as a separate component, or both. Suitable amounts of stabilizer can be between 1 ppm to 9000 ppm, based on hydrogen peroxide solution weight.

In one embodiment, 3-HPPA is made through the acid-catalyzed equilibrium reaction of 3-hydroxy propionic acid with a source of peroxide. It should be appreciated that additional species could be present along with the starting 3-hydroxypropionic acid. Such additional species could include acrylic acid, and the dimer, trimer, and/or polymers of 3-hydroxypropionic acid. If acrylic acid is present, the weight ratio of acrylic acid to 3-hydroxypropionic acid is from 1:80 to 1:5, preferably from 1:30 to 1:10. If the dimer and/or higher order species are present, the weight ratio of dimer to 3-hydroxypropionic acid is from 1:30 to 1:1, preferably from 1:10 to 1:5. It should also be appreciated that, if additional species are present, the corresponding peroxy acids of such species will also be present in the equilibrium mixture.

The peroxy acids of the present technology have been found to have antimicrobial properties against a wide variety of microbial targets when tested according to standardized efficacy evaluation protocols, making them useful in disinfecting and sanitizing compositions. In some embodiments, the peroxy acids of the present technology are present in the compositions in an amount effective for killing one or more microbial targets, including Gram negative bacteria, such as *Pseudomonas aeruginosa* (Pa), *Campylobacter jejuni* (Cj), *Salmonella enterica* (Se) and *Escherichia coli* (Ec); Gram positive bacteria, such as *Staphylococcus aureus* (Sa) and *Listeria monocytogenes* (Lm); molds such as *Penicillium marneffei* (Pm), *Tricophyton mentagrophytes* (Tm) and *Aspergillus niger* (An); yeasts such as *Candida albicans* (Ca); and green algae, such as *Chlorella vulgaris* (Cv), and blue-green algae. For example, 3-HPPA has been found to pass the efficacy tests against spores of *Clostridium difficile* (Cd) by the current EPA test methods of Antimicrobial Testing Methods & Procedures: Quantitative Disk Carrier Test Method (QCT-2) Modified for Testing Antimicrobial Products Against Spores of *Clostridium difficile* (ATCC 43598) on Inanimate, Hard, Non-porous Surfaces:MB-31-03, and against Sa and Pa by the current AOAC Use Dilution Test for Testing Disinfectants (Association of Official Analytical Chemists (AOAC) Methods 955.15 and 964.02): MB-05-13, (commonly referred to as the AOAC Use-Dilution Method), and against Sa and Ec by the current AOAC method, Method 960.09: AOAC Germicidal and Detergent Sanitizing Action of Disinfectants. 2013.

The peroxy acids of the present technology can be used in a wide variety of compositions and applications, including sanitizing, disinfecting, sporicidal, fungicidal, virucidal, algaecidal and mildewcidal compositions, deodorizing, bleaching and oxidizing, detergents and cleaners (laundry, home cleaner, hair care), and skin cleansers. In some embodiments, the peroxy acids of the present technology can be formulated into compositions for use in killing microorganisms on a food processing surface, directly on the surface of a food product, and on other surfaces in areas such as in kitchens, bathrooms, hospitals, assisted living facilities, schools, restaurants, cafeterias, factories and food plants. In some embodiments, the peroxy acids can be formulated into compositions for use as cleaners that are directly applied to foods, including fruits and vegetables. In other embodiments, the peroxy acids can be used in compositions to control microbial growth in oil field treatment solutions, pulp and paper applications, and cooling water systems. In still further embodiments, the peroxy acids disclosed herein can be formulated into compositions used to treat waste water and other industrial process streams such as heaters, cooling towers, and boilers for odor control and bleach paper pulp.

Additional components can be combined with the peroxy acids to prepare the compositions depending on the end use. For example, one or more surfactants can be added to the compositions to improve cleaning, detergency, and/or microbiocidal efficacy. The surfactants can be anionic, nonionic, amphoteric/zwitterionic, cationic or combinations thereof. Examples of useful surfactants include, but are not limited to, alkyl sulfates, alkyl ether sulfates, sulfonates, alcohol ethoxylates, alkyl amine oxides, betaines, sarcosinates, and quaternary ammonium compounds. Particularly useful surfactants include alcohol ethoxylate surfactants, for example Bio-soft® ET-65 (ethoxylated C10-C14 alkyl alcohols) or Bio-Soft® N1-9 (ethoxylated C11 alkyl 9EO alcohol), both available from Stepan Company, Northfield, Ill. Particularly suitable quaternary ammonium compounds include dialkyldimethyl ammonium methyl sulfate. In some embodiments, the ratio of peroxy acid to quaternary ammonium compound can be 10:1 to 1:20.

Other components or additives can also be included in the compositions. Additional components can include pH adjustment agents, polymers for viscosity adjustment, electrolytes for enhancement of surfactant detergency, chelators for improvement of surfactant detergency and of cationic surfactant efficacy, fragrances for different attractive smells, dyes for pleasing color, and other functional ingredients.

Compositions according to the present technology can be supplied in different forms depending on the desired end use. In some embodiments, the composition is in a ready-to-use form that can be used without dilution. In accordance with other embodiments of the present technology, the composition comprising the peroxy acid is a dilutable concentrate product. As defined above, a dilutable concentrate product is a product that needs to be diluted with a diluent (e.g., water) in a ratio of about, for example but not limited to, 1:256, 1:128, 1:64, or 1:32 before it can be applied to articles or surfaces to be disinfected or sanitized. Depending on the intended dilution ratio, the concentration of actives in the dilutable concentrate product can vary. For example, the dilutable concentrate composition can contain from about 0.001% to about 15.0% by weight, alternatively from about 0.01% to about 10%, alternatively about 0.1% to about 5% of the peroxy acid, based on the total weight of the concentrate. The dilutable concentrate composition can be diluted using any of the delivery vehicles available in the art. For example, water, either de-ionized or normal tap water, organic solvent (ethanol, propanol, glycols), or a mixture thereof, can be used as the diluent. The concentrate composition can be diluted by an amount of diluent sufficient to obtain a final concentration of peroxy acid of about 1 to about 10000 ppm, alternatively about 5 to about 9000, alternatively about 50 ppm to about 6000 ppm, alternatively about 100 ppm to about 5000 ppm, alternatively about 2 ppm to about 10,000 ppm, alternatively about 10 ppm, about 15 ppm, about 20 ppm, about 25 ppm, about 30 ppm, about 40 ppm, about 50 ppm, about 60 ppm, about 75 ppm, about 80 ppm, about 90 ppm, about 100 ppm, about 125 ppm, about 130 ppm, about 140 ppm, about 150 ppm, about 160 ppm, about 175 ppm, about 180 ppm, about 190 ppm, or about 200 ppm to about 9,000 ppm, alternatively about 150 ppm to about 8800 ppm.

The presently described technology and its advantages will be better understood by reference to the following examples. These examples are provided to describe specific embodiments of the present technology. By providing these specific examples, it is not intended to limit the scope and spirit of the present technology. It will be understood by those skilled in the art that the full scope of the presently described technology encompasses the subject matter defined by the claims appended to this specification, and any alterations, modifications, or equivalents of those claims.

EXAMPLES

The bacteria used in the examples include:
Pa: a highly resistant Gram negative bacterium, which is often used to substantiate the efficacy of disinfectants against Gram positive bacteria, available from American Type Culture Collection (ATCC), Manassas, Va. as ATCC 15442;
Sa: a Gram positive bacterium, which is often used to substantiate the efficacy of disinfectants against Gram negative bacteria, available as ATCC 6538;
Cd: a Gram positive, spore forming bacterium, which can be used to substantiate sporical efficacy, available as ATCC 43598;
Ec: one of the main species of bacteria that live in the lower intestines of mammals (fecal bacteria), commonly used as an indicator organism for potential contamination of a surface with human intestinal disease causing bacteria used to substantiate the efficacy against food borne disease causing bacteria, available as ATCC 11229.

Example 1

Comparison of Peracid Odor and Stability Relationship to Positions of Substituted Group Peracids were generated at room temperature or below from a reaction mixture comprising water, $H_2O_2$, the corresponding carboxylic acid, and $H_2SO_4$ as a catalyst. The $H_2O_2$ used is commercially available from Arkema under the tradename Perxoal 50EG and includes a small amount of stabilizer. The reaction proceeded until equilibrium was reached, in accordance with the reaction scheme recited above. The starting carboxylic acids were acetic acid, 3-hydroxy propanoic acid, 3-chloro-propanoic acid, 2-hydroxy-acetic acid (glycolic acid), 2-hydroxy-propanoic acid (lactic acid) and 2-oxo-propanoic acid. The 3-hydroxy propanoic acid and 3-chloro-propanoic acid generated non alpha-substituted peracids that are examples of the present technology. The other starting carboxylic acids generated peracids that are not within Formula 1 or Formula 2 and are comparative peracid examples. The starting reaction formulations are shown in Table 1.

Each of the resulting peracids were evaluated for odor. In addition, the resulting peracids were evaluated for stability using a standard titration method known to those skilled in the art. The results of the odor and stability testing are provided in Table 2.

TABLE 2

Peracid Generation, Property & Stability Relationship to Positions of Substituted Group

| Starting reagents | AA | 3-HPA | AA | 3-HPA | 3-CIPA | 2-HAA | 2-HPA | 2-OPA |
|---|---|---|---|---|---|---|---|---|
| Organic acid | 17.00% | 20.00% | 20.00% | 20.00% | 20.00% | 20.00%/ | 20.00% | 20.00% |
| $H_2O_2$ | 8.5% | 7.8% | 7.50% | 7.50% | 7.50% | 7.50% | 7.50% | 7.50% |
| $H_2SO_4$ | 0% | 0% | 1.00% | 1.00% | 1.00% | 1.00% | 1.00% | 1.00% |
| DI water | 74.50% | 72.2% | 71.50% | 71.50% | 71.50% | 71.50% | 71.50% | 71.50% |

TABLE 2-continued

Peracid Generation, Property & Stability Relationship to Positions of Substituted Group

| Products | PAA | 3-HPPA | PAA | 3-HPPA | 3-CIPPA | 2-HPAA | 2-HPPA | 2-OPPA |
|---|---|---|---|---|---|---|---|---|
| Peracid at day 6 | | | 2.290% | 0.735% | 0.910% | 0.770% | 1.690% | 0.290% |
| Peracid at day 13 | 1.44% | Not Detectable | 2.270% | 0.720% | 0.876% | 0.740% | 1.530% | 0.030% |
| Peracid loss/day | No test | N.A. | 0.131% | 0.272% | 0.534% | 0.606% | 1.381% | 12.644% |
| Smell | pungent | N.A. | pungent | negligible | reduced | reduced | negligible | reduced |

Organic Acid Abbreviations:
AA: acetic acid; 3-HPA: 3-hydroxypropanoic acid; 3-CIPA: 3-chloropropanoic acid;
2-HAA: 2-hydroxyacetic acid or glycolic acid; 2-HPA: 2-hydroxypropanoic acid or lactic acid;
2-OPA: 2-oxopropanoic acid or pyruvic acid
Organic Peracid Abbreviations:
PAA: peracid from AA; 3-HPPA: peracid from 3-HPA; 3-CIPPA: peracid from 3-CIPA 2-HPAA: peracid, perglycolic acid, from 2-HAA; 2-HPPA: peracid, perlactic acid, from 2-H PA;
2-OPPA: peracid from 2-OPA From Table 2, it can be seen that an acidic catalyst may be needed in order to achieve a reaction rate capable of generating an appreciable concentration of 3-HPPA.

From Table 2, it can also be seen that, when there is a substituted group in both the α-/2-position and non-α-position or 3-position, the smell is reduced for the resulting peracid. The peracids of the present technology, having a substituted group at the non-α- or at 3-position (3-HPPA and 3-CIPPA), had better stability than the peracids having the substituted group at the α-position or 2-position, as demonstrated by the lower peracid loss per day for the 3-HPPA and 3-CIPPA. In general, stability of peracids also depend on pH, the quality of $H_2O_2$ (for example stabilizers, if any present, type and amount thereof), and impurities contained in each reagent and DI water. In the present examples, the same stabilized $H_2O_2$ and DI water were used for each reaction mixture, and the presence of 1% $H_2SO_4$ in the reaction mixture yielded a similar final pH for each peracid. The difference in stability can therefore be attributed to the different positions of the substituted groups. The peracid with no substituted group, namely peracetic acid (PAA), has the best stability, but the strongest odor.

Example 2

Different formulations containing 3-HPPA at different concentrations were prepared and evaluated for sporicidal efficacy against Cd. The 3-HPPA formulations were also compared to the sporicidal efficacy of different formulations containing peracetic acid (PAA). The test procedure for evaluating sporicidal efficacy was in accordance with the EPA test method in place in 2015: Quantitative Disk Carrier Test Method (QCT-2) Modified for Testing Antimicrobial Products Against Spores of Clostridium difficile (ATCC 43598) on Inanimate, Hard, Non-porous Surfaces (MB-31-03). This method mandates the presence of a high level of organic soil. The formulations, concentrations, contact times, and water hardness used in this Example are shown in Table 3. Table 3 also shows the results of the efficacy testing.

TABLE 3

Sporicidal Efficacy against Cd (ATCC 43598) of Peracids

| | Peracid Active: ppm | Contact time: minute | Water Hardness: ppm | Initial carrier count in Log | $Log_{10}$ reduction |
|---|---|---|---|---|---|
| PAA alone | 1844 | 2 | 400 | 6.27 | 4.76 |
| | 2500 | 4 | 400 | 6.34 | <4.37 |
| | 5000 | 4 | 400 | 6.51 | 6.39 |
| PAA + 2500 ppm DMS[1] | 2500 | 4 | 400 | 6.34 | >4.91 |
| PAA + 2500 ppm Bio-Soft N1-9 | 2500 | 4 | 400 | 6.34 | >5.28 |
| PAA + 1250 ppm DMS & 1250 ppm Bio-Soft N1-9 | 2500 | 4 | 400 | 6.34 | ≥6.34 |
| 3-HPPA | 2572 | 3 | 400 | 6.38 | <3.08 |
| | 2572 | 10 | 400 | 6.38 | 3.67 |
| | 3500 | 5 | 400 | 6.51 | 3.21 |
| | 8800 | 10 | no dilution | 6.17 | ≥6.17 |
| 3-HPPA + 1250 ppm DMS & 1250 ppm Bio-Soft N1-9 | 3500 | 5 | 400 | 6.51 | 3.81 |

[1]DMS: Dialkyldimethylammonium methyl sulfate available from Stepan Company.
Bio-SoftN1-9: alcohol ethoxylate nonionic surfactant available from Stepan Company.

From Table 3 it can be seen that for PAA, when the active concentration is increased from 1844 to 5000 ppm, the efficacy is increased. At 2500 ppm PAA and 4 minute contact time, the addition of 1250 ppm DMS quat and nonionic surfactant helps to enhance the efficacy from 4.37 to 6.34 log reduction.

For 3-HPPA, the results show that an increase in active level or contact time, or both, helps to enhance the efficacy. The results also indicate that at an active amount of 3500 ppm, the addition of 1250 ppm of DMS quat and Bio-Soft N1-9 helps to raise the efficacy from a log reduction of 49% to a log reduction of 58.5%. At an active level of 8800 ppm, 3-HPPA passes the EPA sporicide efficacy test, allowing it to be claimed as sporicidal against Cd.

Example 3

In this Example, 3-HPPA was evaluated for biocidal efficacy against Sa, Pa, and Ec using three different test methods. PAA was also evaluated for biocidal efficacy for comparison. The test methods were performed using 400 ppm of hard water as diluent, in the presence of 5% organic matter. The efficacy results are shown in Table 4.

TABLE 4

Antibacterial Efficacy of PAA and 3-HPPA

| | Peracid Active: ppm | Contact time: minute | Methods | Organism Type | Initial carrier count in Log | Efficacy (Method A) | Efficacy (Method A+) |
|---|---|---|---|---|---|---|---|
| PAA | 750 | 1 | A & A+ | Sa | 6.97 | 0/20 | >99.9999% |
| | | | | Pa | 6.00 | 0/20 | >99.9999% |
| 3-HPPA | 800 | 3 | A+ | Sa | 6.64 | 0/3 | >99.9999% |
| | | | | Pa | 6.33 | 0/3 | >99.9999% |
| | 600 | 3 | A | Sa | 6.579 | 0/60 pass | |
| | 800 | 3 | A | Pa | 6.485 | 3/60 pass | |

| | | | | | | Efficacy (Method B) |
|---|---|---|---|---|---|---|
| | 200 | 0.5 | B | Sa | 8.39 | >99.999% |
| | | 1.0 | | | | >99.999% |
| | 200 | 0.5 | B | Ec | 8.17 | >99.999% |
| | | 1.0 | | | | >99.999% |

Method A: AOAC Use Dilution test for Disinfectants (Official Methods of Analysis. Methods 955.15—*Staphylococcus aureus*. Method 964.02—*Pseudomonas aeruginosa*. Posted September 2013). Killing efficacy is a qualitative result, reported as number of tubes showing microbial growth and total number carriers tested.

Method A+: modified quantitative AOAC Use Dilution test for Disinfectants (Official Methods of Analysis. Methods 955.15—*Staphylococcus aureus*. Method 964.02—*Pseudomonas aeruginosa*. Posted September 2013). The number of surviving organisms on each carrier was quantitatively determined after the indicated contact time. No growth observed on the solid recovery medium means no survivors present on the carriers after exposure to the antimicrobial composition. A kill rate of 99.9999% is equivalent to a 6 log kill.

Method B: Method 960.09: AOAC Germicidal and Detergent Sanitizing Action of Disinfectants. 2013. Killing efficacy is a quantitative result, reported as percent reduction in microbial counts after exposure to the antimicrobial.

The results in Table 4 show that traditional PAA is efficacious against Sa and Pa at 750 ppm active in 1 minute using the current EPA UDT/MB-05-13 test method. The results in Table 4 also show that 3-HPPA is efficacious against both Gram positive and negative organisms, Sa and Pa, at 800 ppm and 3 minutes by a modification of the current EPA UDT/MB-05-13 test method. The results further show that 3-HPPA is efficacious against Sa and Pa at 600 ppm active and 800 ppm active, respectively, in 3 minutes using the EPA UDT/MB-05-13 test method. 3-HPPA also meets the EPA requirement for efficacy for the current EPA Method 960.09 against Sa and Ec at 200 ppm active at 30 seconds. The results in Table 4 clearly establish 3-HPPA is an effective antibacterial ingredient.

Example 4

In this Example, 3-HPPA was evaluated for anti-microbial efficacy against Sa and Pa using the ASTM E1153-14 Standard Test Method for Efficacy of Sanitizers Recommended for Inanimate, Hard, Nonporous Non-Food Contact Surfaces. In the ASTM E1153-14 test, killing efficacy is a quantitative result, reported as percent reduction in microbial counts after exposure to the antimicrobial. The test method was performed at a water hardness of 400 ppm and at a soil load of 5%. The efficacy results are shown in Table 5.

TABLE 5

3-HPPA anti-microbial efficacy at 400 ppm hard water, and 5% soil load

| Method | Organism | Contact time: minutes | 3-HPPA active concentration: ppm | Initial carrier count in log | Results |
|---|---|---|---|---|---|
| Non-food contact surface sanitizer | Sa | 3 | 800 | 6.676 | >99.999%**, pass |
| | Pa | 3 | 800 | 6.008 | >99.999%**, pass |

**ASTM E1153-14 Standard Test Method for Efficacy of Sanitizers Recommended for Inanimate, Hard, Nonporous Non-Food Contact Surfaces.

The results in Table 5 show that 3-HPPA passes the ASTM E1153-14 Standard Test Method for both Sa and Pa.

The property information in Table 2, and the antimicrobial results in Tables 3, 4 and 5 show that non-alpha-substituted peracids of the present technology are odorless, stable, water soluble peracids that provide excellent antimicrobial efficacy and can be used as sporicidal as well as bactericidal compounds. The results also show that additional surfactants can be used to enhance antimicrobial efficacy.

The present technology is now described in such full, clear and concise terms as to enable a person skilled in the art to which it pertains, to practice the same. It is to be understood that the foregoing describes preferred embodiments of the present technology and that modifications can be made therein without departing from the spirit or scope of the present technology as set forth in the appended claims.

What is claimed is:

1. A composition comprising:
   water, and
   an antimicrobial agent that is a non-α-substituted water soluble low odor peracid having the structure of Formula 1:

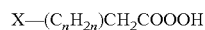

$$X-(C_nH_{2n})CH_2COOOH \qquad \text{Formula 1}$$

where n=1, and
X is OH.

2. The composition of claim 1, wherein the composition is a concentrate and the peracid concentration is from about 0.001% to about 15% by weight, based on the total weight of the concentrate.

3. The composition of claim 2, wherein the peracid concentration is from about 0.01% to about 10% by weight.

4. The composition of claim 2, wherein the peracid concentration is from about 0.1% to about 5% by weight.

5. The composition of claim 2, wherein the peracid concentration after dilution is from 1 to 10,000 ppm.

6. The composition of claim 2, wherein the peracid concentration after dilution is from 100 to 5000 ppm.

7. The composition of claim 1, wherein the composition further comprises at least one surfactant selected from the group consisting of anionic, nonionic, amphoteric, zwitterionic, and cationic surfactants, and combinations thereof.

8. The composition of claim 7, wherein the at least one surfactant comprises an alcohol ethoxylate nonionic surfactant.

9. The composition of claim 8, wherein the alcohol ethoxylate surfactant comprises an ethoxylated C10-C14 alkyl alcohol.

10. The composition of claim 7, wherein the at least one surfactant comprises a cationic quaternary ammonium compound.

11. The composition of claim 10, wherein the quaternary ammonium compound is dialkyldimethyl ammonium methyl sulfate.

12. The composition of claim 1, wherein the composition is a fungicide or a sporicide.

13. A method of making a water soluble, low odor, non-alpha substituted peroxy acid having the structure of the Formula 1

$$X-(C_nH_{2n})CH_2COOOH \qquad \text{Formula 1}$$

where n=1 and X is OH, comprising the steps of:
   a) providing a non-alpha substituted carboxylic acid that is 3-hydroxy-propanoic acid;
   b) providing hydrogen peroxide;
   c) reacting the non-alpha substituted carboxylic acid and the hydrogen peroxide in an aqueous medium in the presence of an acid catalyst until the non-alpha-substituted peroxy acid forms and is in equilibrium with the non-alpha substituted carboxylic acid and the hydrogen peroxide.

14. The method of claim 13, wherein the acid catalyst is selected from sulfuric acid, methanesulfonic acid, hydrochloric acid, and nitric acid.

15. The method of claim 13, wherein the acid catalyst comprises sulfuric acid.

16. The composition of claim 1, wherein the composition provides a killing efficacy of at least 99.999% for at least one microbial target, as measured by Association of Official Analytical Chemists (AOAC) Use-Dilution Method, AOAC Method 960.09, or ASTM E1153-14 Test Method.

17. The composition of claim 16, wherein the microbial target is gram negative or gram positive bacteria.

18. The composition of claim 16, wherein the bacteria is *Escherichia coli*, *Pseudomonas aeruginosa*, or *Staphylococcus aureus*.

* * * * *